(12) United States Patent
Farooqui (10) Patent No.: US 7,654,382 B2
(45) Date of Patent: Feb. 2, 2010

(54) TABLE DRIVE SYSTEM

(75) Inventor: Asghar Ali Farooqui, Bangalore (IN)

(73) Assignee: General Electric Co., Schenectady, NY (US)

( * ) Notice: Subject to any disclaimer, the term of this patent is extended or adjusted under 35 U.S.C. 154(b) by 387 days.

(21) Appl. No.: 11/690,910

(22) Filed: Mar. 26, 2007

(65) Prior Publication Data

US 2008/0235873 A1    Oct. 2, 2008

(51) Int. Cl.
*B65G 47/34* (2006.01)
(52) U.S. Cl. ................... 198/468.9; 384/45
(58) Field of Classification Search .......... 198/468.9, 198/468.01, 594, 595, 812; 414/218; 384/43, 384/44, 45
See application file for complete search history.

(56) References Cited

U.S. PATENT DOCUMENTS

| | | | | |
|---|---|---|---|---|
| 3,837,470 | A | * | 9/1974 | Dunkin ........................ 198/812 |
| 4,681,506 | A | * | 7/1987 | Teramachi ............... 198/468.9 |
| 4,761,000 | A | * | 8/1988 | Fisher et al. .................... 5/608 |
| 6,131,214 | A | * | 10/2000 | Moenning et al. ........... 198/782 |
| 6,309,107 | B1 | * | 10/2001 | Ueki et al. ..................... 384/45 |
| 6,712,512 | B2 | * | 3/2004 | Teramach et al. ............. 384/45 |

\* cited by examiner

*Primary Examiner*—James R Bidwell (57) ABSTRACT

A table drive system comprising a first drive assembly configured for moving a support table in a first direction, a second drive assembly configured for moving the support table in a second direction and a drive motor coupled to the first drive assembly and the second drive assembly is provided. The drive motor is configured to drive the first drive assembly and the second drive assembly.

21 Claims, 9 Drawing Sheets

TABLE DRIVE SYSTEM

FIELD OF INVENTION

This invention relates generally to a table drive system and more particularly to a drive system for moving a table in multiple directions.

BACKGROUND OF THE INVENTION

Patient positioning systems engage and support a medical subject undergoing a medical procedure such as a diagnostic procedure, a therapeutic procedure and a surgical procedure. Typically a patient positioning system comprises a support table on which the medical subject is positioned and a drive system for positioning the support table. The process of aligning the medical subject for the medical procedure involves motion of the support table along multiple axis. Therefore, the drive system configured for positioning the support table is desired to be capable of moving the support table along multiple axis.

For moving the support table along multiple axis, the drive system can comprise a plurality of drive assemblies. Each drive assembly can be configured to drive the motion of the support table along a single axis. Conventional methodology of achieving motion of the support table along multiple axis comprises a screw drive assembly for driving motion along X-axis, a rack and pinion drive assembly for driving motion along Y-axis, and a hydraulic drive assembly for driving motion along Z-axis.

The patient positioning system conventionally comprises multiple drive motors as each drive assembly is coupled to a single drive motor in a very complex and inaccessible compact way. The drive motors are expensive and hence using a plurality of independent drive motors may not be an economical option. Moreover, using a plurality of independent drive motors requires sufficient space to facilitate appropriate assembly, maintenance and repair. Another drawback of using multiple drive motors is that the capacity of each drive motor is often underutilized in terms of functioning and idle time.

Hence, there exists a need to provide a simple, compact, reliable, serviceable and cost effective drive system for a patient positioning system.

SUMMARY OF THE INVENTION

The above-mentioned shortcomings, disadvantages and problems are adressed herein which will be understood by reading and understanding the following specification.

In an embodiment, a table drive system is provided. The table drive system comprises a first drive assembly configured for moving a support table in a first direction, a second drive assembly configured for moving the support table in a second direction and a drive motor coupled to the first drive assembly and the second drive assembly. The drive motor is configured to drive the first drive assembly and the second drive assembly.

In another embodiment, a drive system for a patient positioning system is provided. The drive system comprises at least two driving members configured for moving a patient support table and a drive motor coupled to the at least two driving members. The drive motor is configured to drive the at least two driving members.

In yet another embodiment, a patient positioning system is provided. The patient positioning system comprises a patient support table, a first drive assembly adapted for moving the patient support table in a first direction, a second drive assembly adapted for moving the patient support table in a second direction and a drive motor coupled to the first drive assembly and the second drive assembly. The drive motor is configured to drive the first drive assembly and the second drive assembly.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
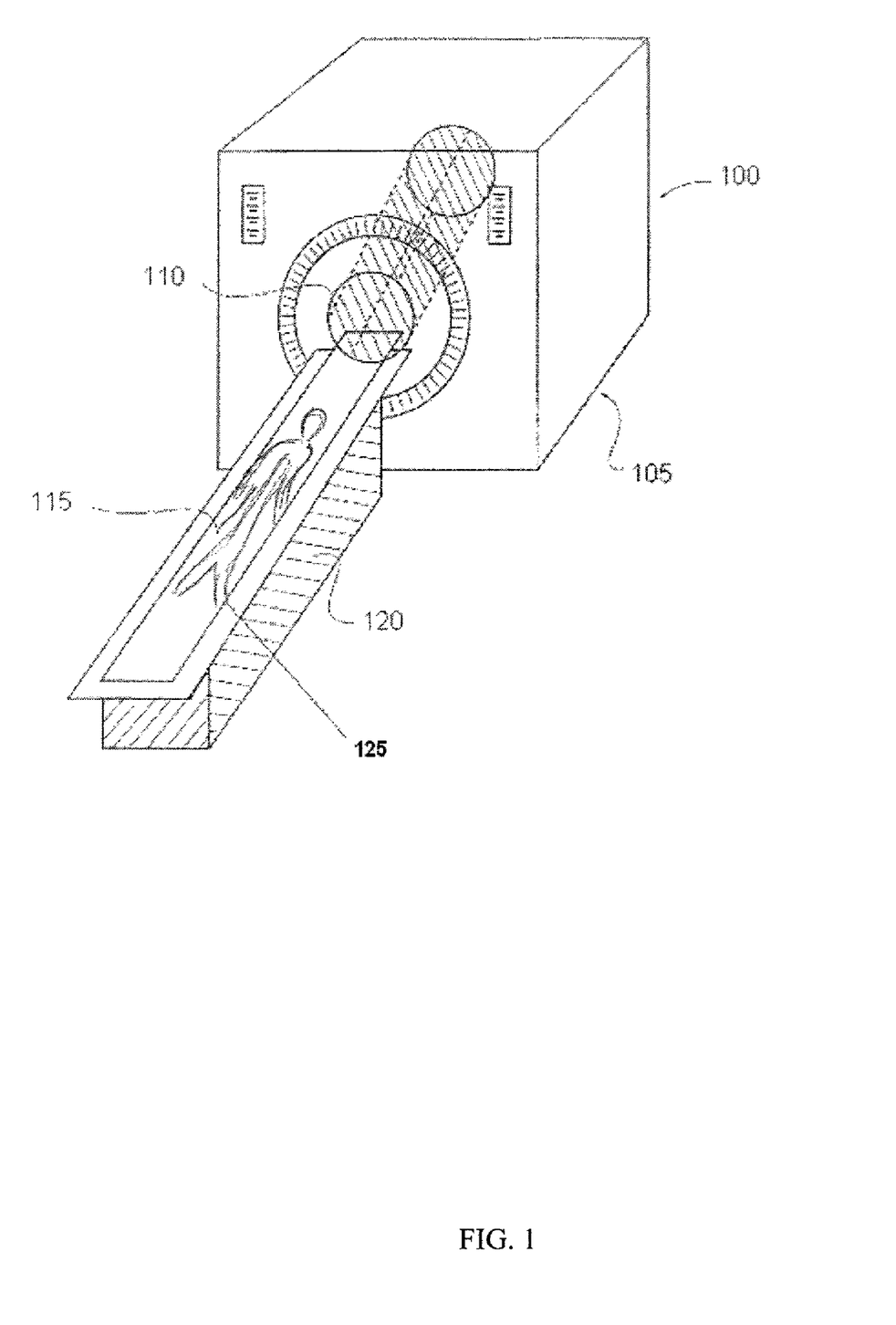
FIG. 1 shows a schematic diagram of an example of an imaging device in an embodiment of the invention.

FIG. 1 shows a schematic diagram of an example of an imaging device 100. The imaging device 100 can be one of a computed tomography device, a positron emission tomography device, a magnetic resonance imaging device, an ultrasound-imaging device, an x ray device, or a combination of such devices. One skilled in the art will however appreciate that, the examples of the imaging device 100 are not limited to the examples mentioned above and the invention shall have full scope of the claims.

The imaging device 100 comprises an imaging gantry 105 that includes a bore or tunnel 110 for receiving a medical subject 115. The medical subject 115 refers to an article, a person or an animal. In one embodiment, as shown in FIG. 1, a patient positioning system 120 for positioning the medical subject 115 in the imaging gantry 105 is provided. The patient positioning system 120 comprises a patient support table 125 for supporting and engaging the medical subject 115. The patient support table 125 can be configured to be displaced to multiple positions along multiple axes to facilitate the positioning of the medical subject 115 for imaging. In one embodiment, the patient support table 125 is configured to displace the medical subject 115 along longitudinal, lateral and vertical directions (which may be referred to as the X, Y or Z-axis directions).

Skilled artisans shall however appreciate that the patient positioning system 120 forming a part of the imaging device 100 is an exemplary embodiment and in general the patient positioning system 120 can be a part of a diagnostic device such as an imaging device 100, a therapeutic device and a surgical device. Further, the positioning system 120 can be either integral with or separate from the imaging gantry 105 in the imaging device 100.

The patient support table 125 may include a table top, a table base, a first roller assembly coupled to the table top and a second roller assembly coupled to the table base. Each roller assembly comprises multiple rollers and a pair of support rails. The support rails may be identical, extended generally parallel to each other and between the opposing sides of the patient support table 125. This is further explained in conjunction with FIG. 4.

Figure 2:
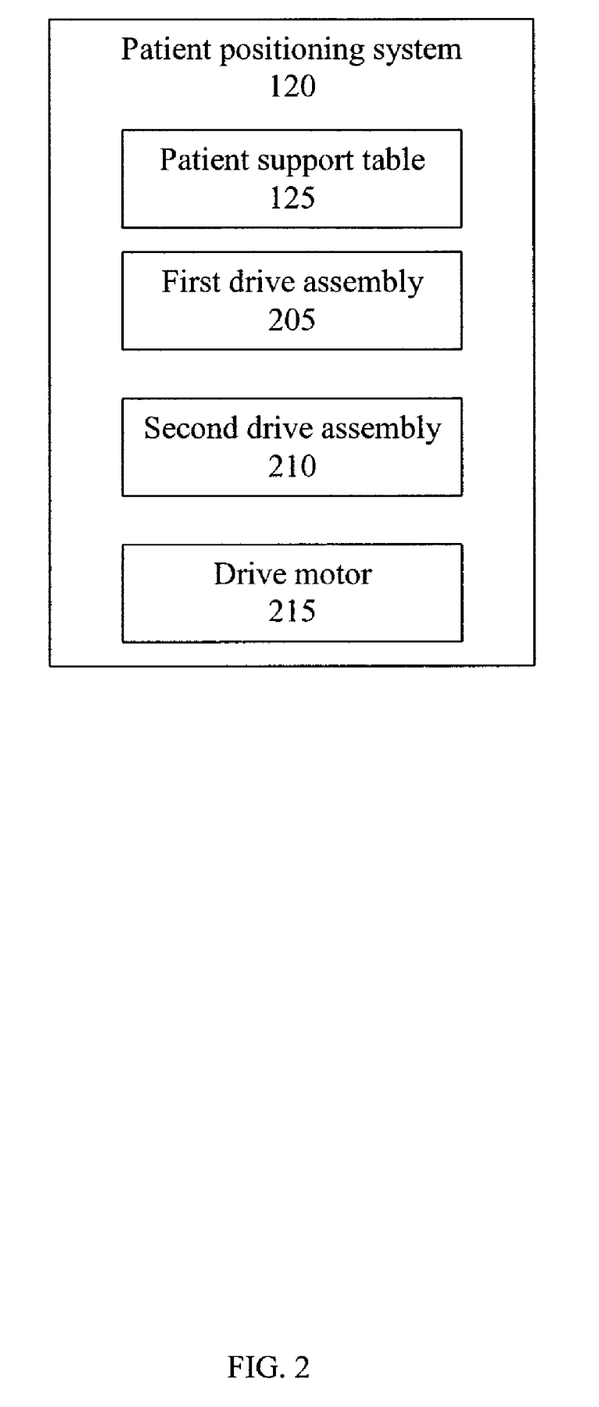
FIG. 2 shows a block diagram of an example of a patient positioning system in an embodiment of the invention.

FIG. 2 depicts a block diagram of the patient positioning system 120 in one embodiment of the invention. The patient positioning system 120 comprises the patient support table 125, a combination of a first drive assembly 205 and a second drive assembly 210, each configured to drive the patient support table 125, and a drive motor 215 coupled to the first drive assembly 205 and the second drive assembly 210, the drive motor 215 being configured to drive the first drive assembly 205 and the second drive assembly 210 to move the patient support table 125 in multiple directions.

Each of the first drive assembly 205 and the second drive assembly 210 can be coupled to the drive motor 215 using a positive drive assembly such as a belt drive assembly or, in other embodiments, a chain drive assembly or a similar drive assembly. The revolution-per-minute (RPM) of the drive motor 215 is in close loop with the first and second drive assemblies 205 and 210 through the belt drive assembly. For example, the first drive assembly 205 can be coupled to the drive motor 215 using a first belt drive assembly and the second drive assembly 210 can be coupled to the drive motor 215 using a second belt drive assembly. This is further explained in conjunction with FIG. 4.

Figure 3:
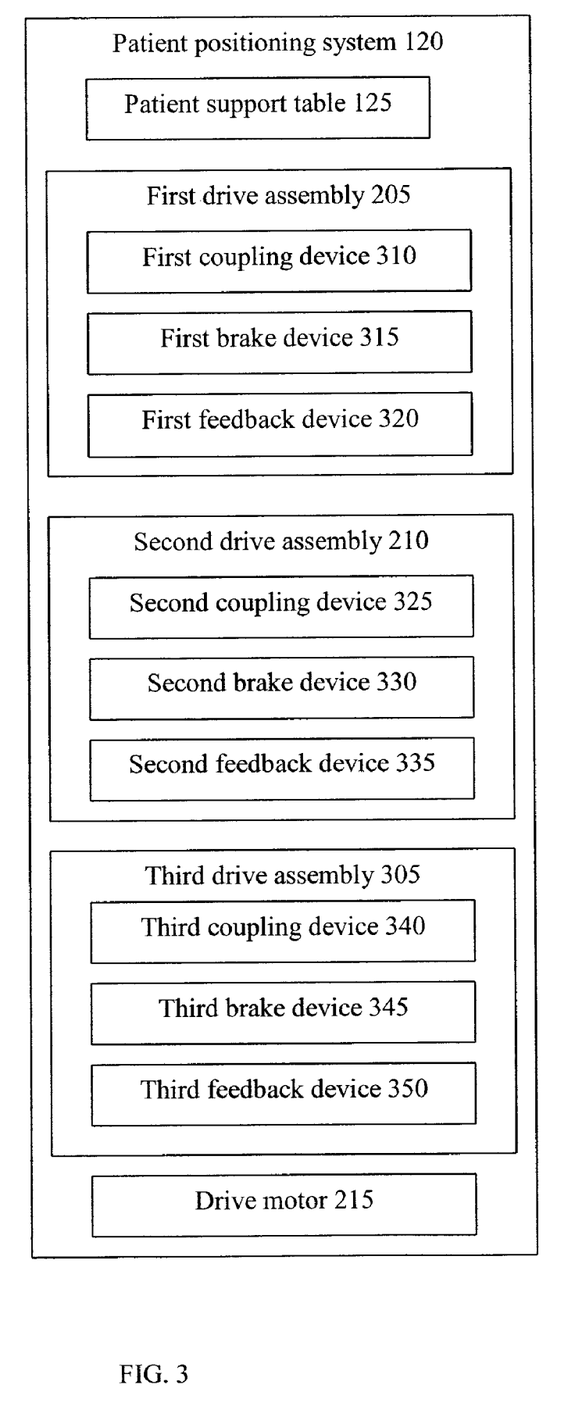
FIG. 3 shows a block diagram of an example of a patient positioning system in another embodiment of the invention.

In another embodiment as shown in FIG. 3, the patient positioning system 120 can further comprise a third drive assembly 305 in combination with the first drive assembly 205 and the second drive assembly 210, and the drive motor 215 can be configured to drive the third drive assembly 305 in addition to the first drive assembly 205 and the second drive assembly 210. In this embodiment, a single drive motor (i.e., 215) is advantageously used to drive three different drive assemblies (i.e., 205, 210 and 305). Skilled artisans shall however appreciate that the number of the drive assemblies in the patient positioning system 120 is not limited and the patient positioning system 120 can comprise a plurality of drive assemblies as claimed in the invention.

The multiple drive assemblies 205, 210 and 305 of the patient positioning system 120 can be configured to drive the patient support table 125 along multiple axis. For example, the first drive assembly 205 can be configured to drive the patient support table 125 in a first direction such as a longitudinal or X direction, the second drive assembly 210 can be configured to drive the patient support table 125 in a second direction such as a lateral or Y direction and the third drive assembly 305 can be configured to drive the patient support table 125 in a third direction such as a vertical or Z direction. An electronic control module may be provided for selectively energizing the respective drive assemblies 205, 210 and 305. Based on operator input, the electronic control module or other switch arrangement can be configured to control which drive assembly 205, 210 or 305 is energized. In one embodiment, each of drive assemblies 205, 210 and 305 is driven only when the other two of drive assemblies 205, 210 and 305 are not driven, thereby limiting the driving requirements needed from the drive motor 215.

The drive motor 215 configured to drive multiple drive assemblies 205, 210 and 305 can be a double-end shaft motor comprising shafts that extend outwardly in opposite directions. Depending on the requirement the drive motor 215 can be one of a stepper, servo and a geared motor driven by AC/DC power. Further, the drive motor 215 can be selected to be rated with maximum torque output. The drive motor 215 with the maximum torque output is capable of moving the patient support table 125 independently along each of the multiple axes. Further, the motion of the patient support table 125 along each axis can be independently controlled with the help of a computer program.

Each of the first drive assembly 205, the second drive assembly 210 and the third drive assembly 305 can be coupled to the drive motor 215 using a coupling device. The coupling device can be generally used in the patient positioning system 120 as a safety device. In the patient positioning system 120 provided in one embodiment, the coupling device can be used for transmission in addition to being used as the safety device. Further, the coupling device when clubbed with a drive assembly provides smooth engagement and eliminates chatter.

Further, each drive assembly 205, 210 and 305 can be directly coupled to a feedback device at a first end and the brake device at a second end. The feedback device provides a greater positioning accuracy whereas the brake device provides safety and imparts a robust design feature to the drive assembly. Accordingly, the first drive assembly 205 comprises a first coupling device 310, a first brake device 315 and a first feedback device 320, the second drive assembly 210 comprises a second coupling device 325, a second brake device 330 and a second feedback device 335 and the third drive assembly 305 comprises a third coupling device 340, a third brake device 345 and a third feedback device 350.

The coupling devices 310, 325 and 340 can be employed to selectively engage multiple drive assemblies 205, 210 and 305 coupled to the drive motor 215 to drive the motion of the patient support table 125 along multiple axis. At a given time, a single coupling device can be actuated to activate the associated drive assembly thereby moving the patient support table 125 along a predetermined axis. During the time when one of the coupling devices (e.g., 310), is engaged with the drive motor 215, the rest of the coupling devices (e.g., 325 and 340) can be disengaged. However, when the patient support table 125 is been driven along one axis, the disengaged coupling devices (e.g., 325 and 340) may be ideally rotating without transmission. In an exemplary embodiment, each coupling device 310, 325 and 340 can be selected to be an electromechanical clutch.

The revolution-per-minute (RPM) of the drive motor 215 is in close loop with the drive assembly 205, 210 or 305 through the feedback device 320, 335 or 350. The feedback device 320, 335 or 350 can be an absolute encoder for providing an indication of an absolute position of the patient support table 125.

The brake device 315, 330 and 345 coupled at another end of each drive assembly 205, 210 and 305 can be configured to bring in redundancy into the patient positioning system 120. Each brake device 315, 330 and 345 coupled to a single drive assembly 205, 210 or 305 can be located to control the motion of the patient support table 125 along a single axis. Each brake device 315, 330 and 345 can be configured to lock the motion of the patient support table 125 at a predetermined position on a selected axis during the time when the motion of the patient support table 125 is initiated in another axis or when the transmission system is engaged with the motion of the patient support table 125 along other axis. In an exemplary embodiment, each brake device 315, 330 or 345 can be selected to be an electro magnetic brake.

Figure 4:
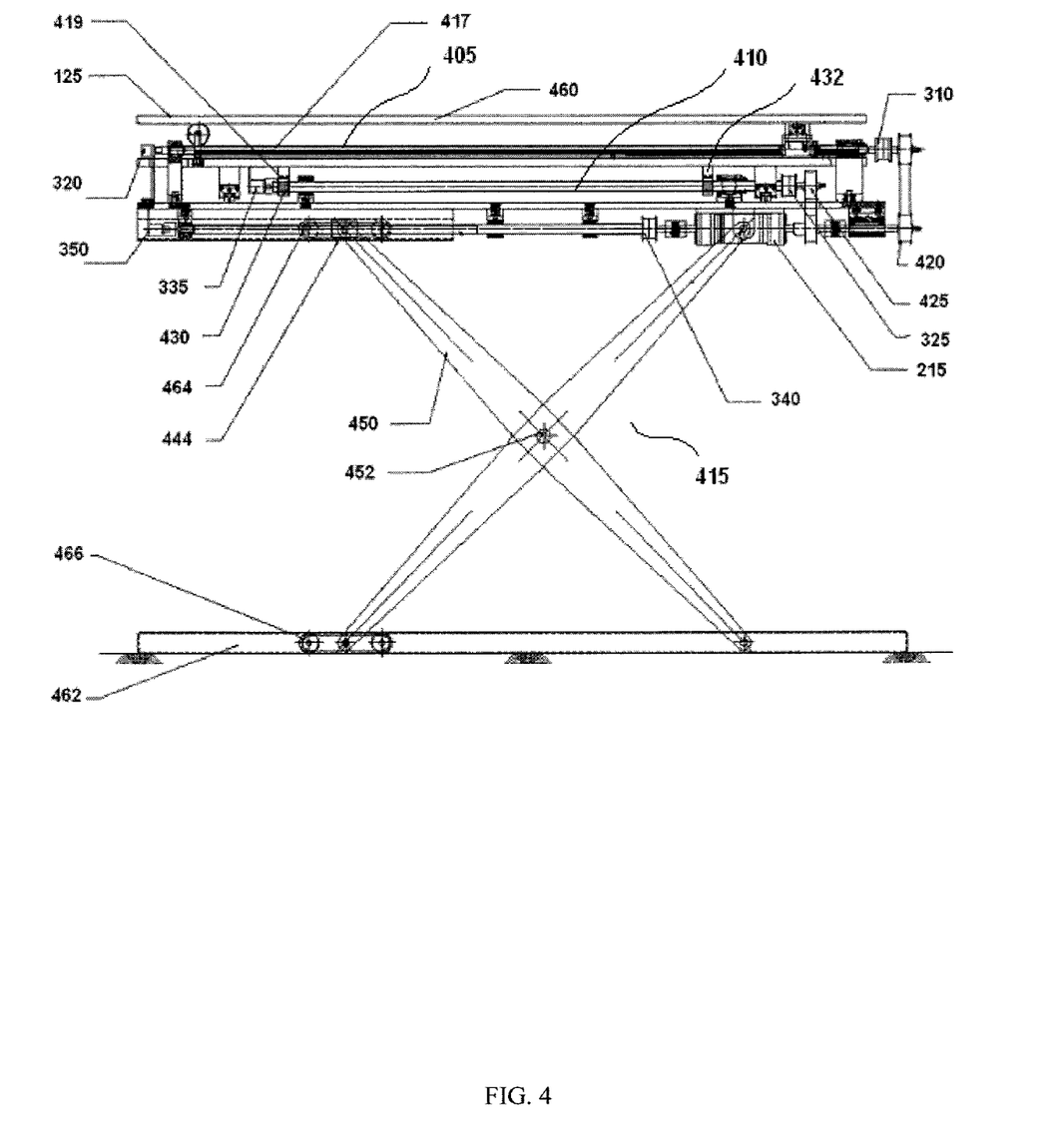
FIG. 4 shows a schematic diagram of an exemplary embodiment of the patient positioning system comprising a double-ended shaft motor coupled to three drive assemblies in one embodiment of the invention.
Figure 5:
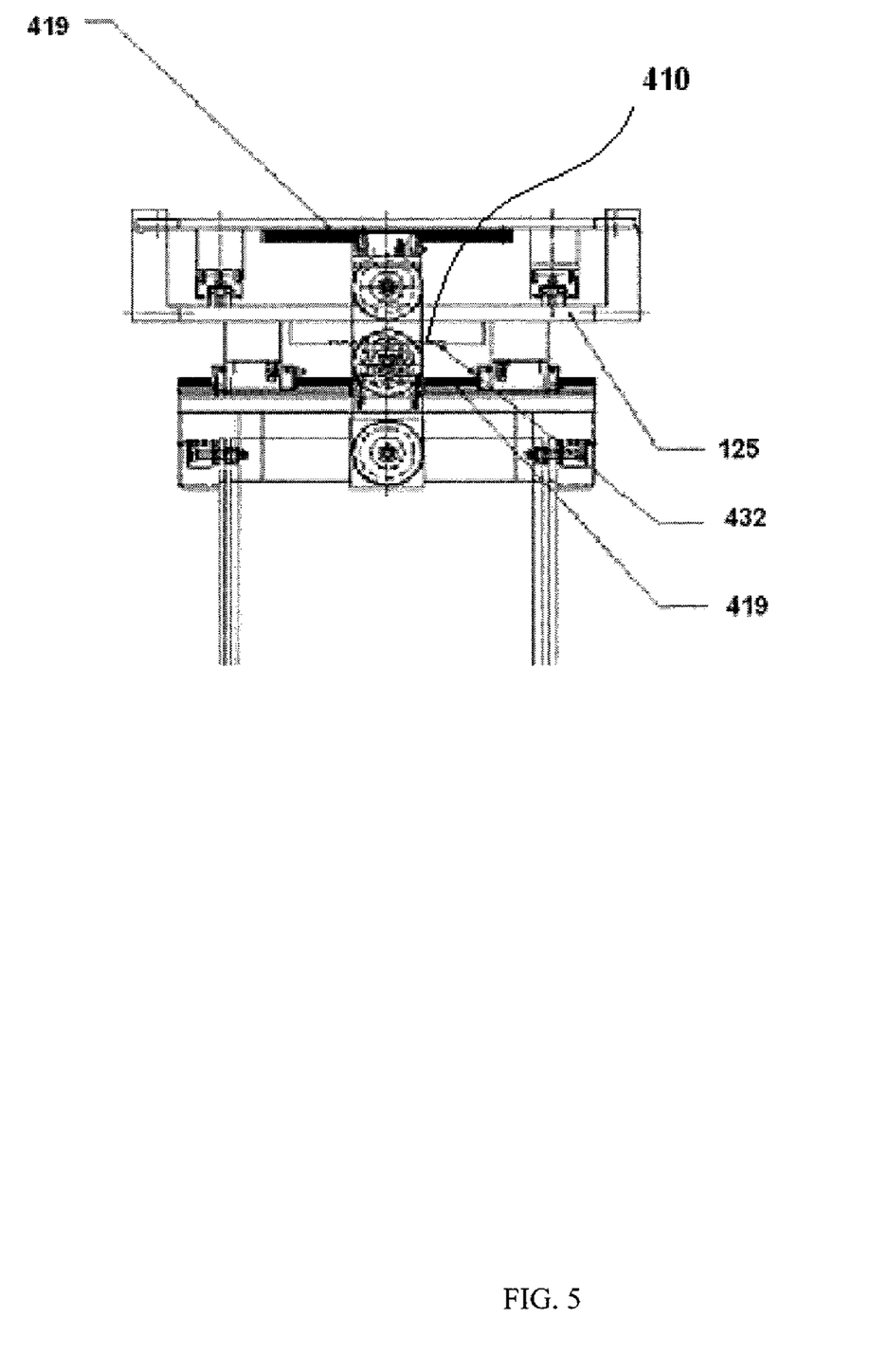
FIG. 5 shows a schematic diagram of the side view of the exemplary embodiment of the patient positioning system shown in FIG. 4.

FIG. 4 and FIG. 5 show the front view and the side view of the patient positioning system 120 depicting the coupling between the drive motor 215 and the three drive assemblies 205, 210 and 305. The first drive assembly 205, the second drive assembly 210 and the third drive assembly 305 can be mounted on a common mounting member (not shown) using a fixture such as, a support bracket, fastened or welded on to the mounting member (not shown). The mounting member (not shown) can be a longitudinal plate for example.

As shown in FIG. 4, the first drive assembly 205 is coupled to the drive motor 215 using the first belt drive assembly 420 comprising a first timer pulley and a first drive belt and the second drive assembly 210 is coupled to the drive motor 215 using the second belt drive assembly 425 comprising a second timer pulley and a second drive belt.

In one exemplary embodiment, the first drive assembly 205 may comprise a screw drive assembly 405, the second drive assembly 210 may comprise a rack and pinion drive assembly 410 and the third drive assembly 305 may comprise a cross bar drive assembly 415. One skilled in the art shall however appreciate that the first drive assembly 205, the second drive assembly 210 and the third drive assembly 305 are not limited by the examples given above and each drive assembly 205, 210 and 305 can be substituted by more viable options.

The screw drive assembly 405 comprises a driving screw 417 and one or more linear motion guides 419. Typically, linear motion guides 419 are linear motion bearings that bear loads to guide the linear motion. The linear motion guide 419 facilitates the driving screw 417 to be in a predetermined position when the patient support table 125 moves along the second direction. Thus, the presence of the linear motion guide 419 adjacent to the driving screw 417 facilitates the motion of the patient support table 125 along the second direction.

The motion of the patient support table 125 along the second direction can be achieved by using a transmission comprising a rack and pinion arrangement. A rack and pinion drive assembly 410 comprises at least one pinion 430 engaged with a rack 432 for transmitting the motion from the drive motor 215 to the patient support table 125 for effecting lateral movement of the patient support table 125.

The at least one pinion 430 is rotatably mounted at the center in the widthwise direction of the patient support table 125 with the rotating axis of the pinion 430 extending horizontally and perpendicularly to the lateral direction of the patient support table 125. The rack 432 movably coupled to the pinion 430 is fixedly mounted at the center in the widthwise direction of the patient support table 125 as extending in the lateral direction of the patient support table 125.

Further, the motion of the patient support table 125 along the third direction can be achieved by using a cross bar drive assembly 415. The cross bar drive assembly 415 converts a linear motion in a horizontal plane to a linear motion in a vertical plane. The cross bar drive assembly 415 can comprise a scissor assembly 450 and an actuator assembly (not shown) for actuating the motion of the scissor assembly 450 in the horizontal plane. The support rails provide for co-operation during the horizontal movement of the scissor assembly 450. The scissor assembly 450 may be slidably mounted between the first roller assembly 464 and the second roller assembly 466. The scissor assembly 450 comprises structural members such as one or more pair of cross bars configured for enabling the movement of the patient support table 125 along the vertical axis. Each pair of cross bars comprises a first cross bar and a second cross bar, the second cross bar being movably coupled to the first cross bar using a pivot 452.

Further, the actuator assembly (not shown) comprises a screw shaft (not shown) coupled to the drive motor 215. The screw shaft (not shown) may be a threaded screw shaft (not shown) with a helical thread set at a given lead or pitch. Positioned on the threaded screw shaft (not shown) are a pair of drive nuts 444 each having a sliding block (not shown) attached thereto. Each drive nut 444 may be rotated relative to the screw shaft (or vice versa) to impart linear motion to either the drive nut 444 or the screw shaft (not shown). Further, the drive nuts 444 may be rotated in opposite direction relative to each other. For example, a clockwise rotation of the screw shaft (not shown) causes a linear movement of the connected drive nuts 444 in a direction axially opposite to each other. An anticlockwise rotation of the screw shaft (not shown) results in an axial movement of each drive nut 444 in a direction opposite to that resulting from the clockwise rotation of the screw shaft (not shown).

As the drive nut 444 and the screw shaft (not shown) rotate relative to each other the sliding blocks (not shown) attached to the drive nuts 444 move along a longitudinal axis of the screw shaft (not shown). As the sliding blocks (not shown) move in the horizontal plane, the cross bars associated with the sliding blocks (not shown) move in a vertical plane. The movement of the cross bars along a vertical axis enables a displacement of the table top 460 with respect to the table base 462. Thus, the patient support table 125 can be configured to move along the vertical axis, based on the rotation of the screw shaft (not shown).

Figure 6:
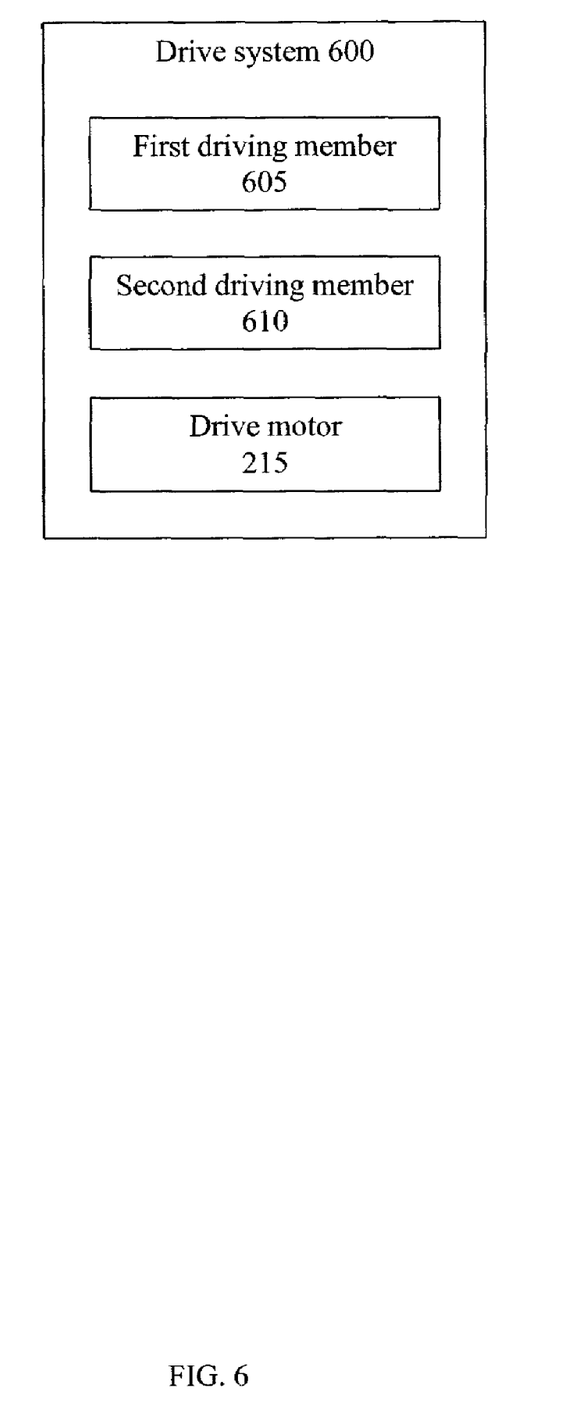
FIG. 6 shows a block diagram of an example of a drive system in an embodiment of the invention.

In another embodiment, a drive system 600 for the patient positioning system 120 is provided as shown in FIG. 6. The drive system 600 comprises at least two driving members namely a first driving member 605 and a second driving member 610 configured for moving the patient support table 125 and a drive motor 215 coupled to the at least two driving members 605 and 610, the drive motor 215 being configured to drive the at least two driving members 605 and 610.

Figure 7:
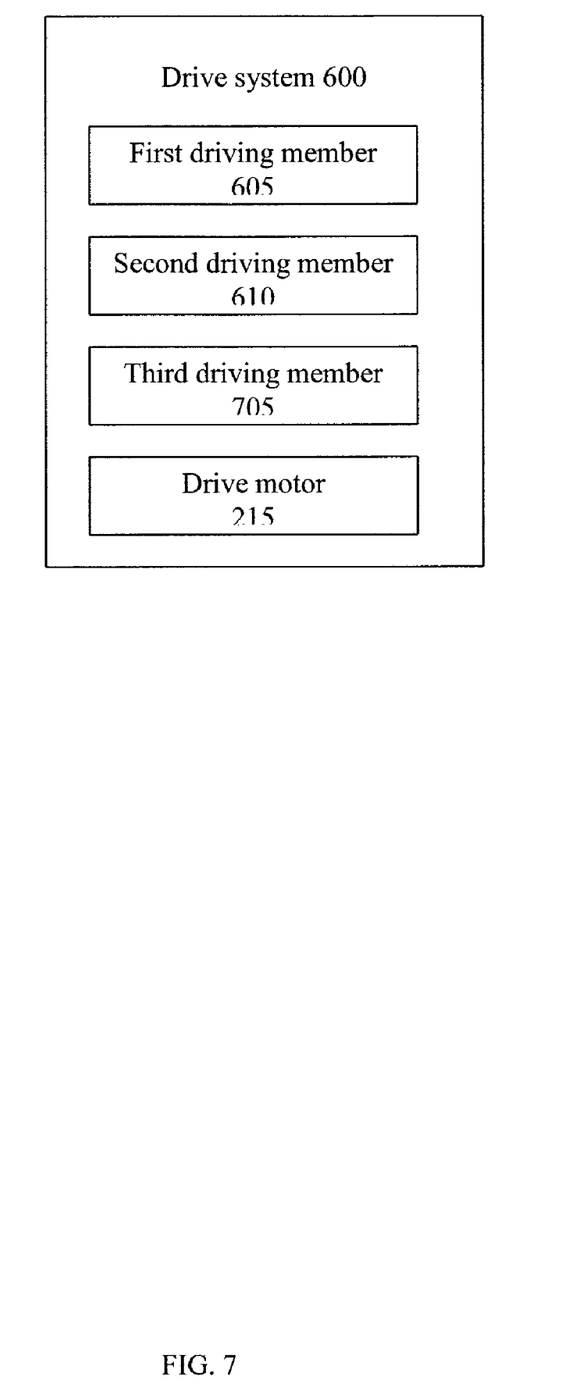
FIG. 7 shows another block diagram of an example of the drive system in another embodiment of the invention.

In another embodiment as shown in FIG. 7, the drive system 600 may further comprise a third driving member 705 and the drive motor 215 can be configured to drive the third driving member 705.

In an exemplary embodiment, the first driving member 605 may comprise a screw drive assembly 405, the second driving member 610 may comprise a rack and pinion drive assembly 410 and the third driving member 705 may comprise a cross bar drive assembly 415.

Skilled artisans shall however appreciate that the number of the driving members is not restricted and the drive system 600 can comprise a number of driving members, the number ranging from two to any number. Accordingly, with the increase in the number of the driving members, the rating of the drive motor 215 configured to drive the driving members can increase.

Figure 8:
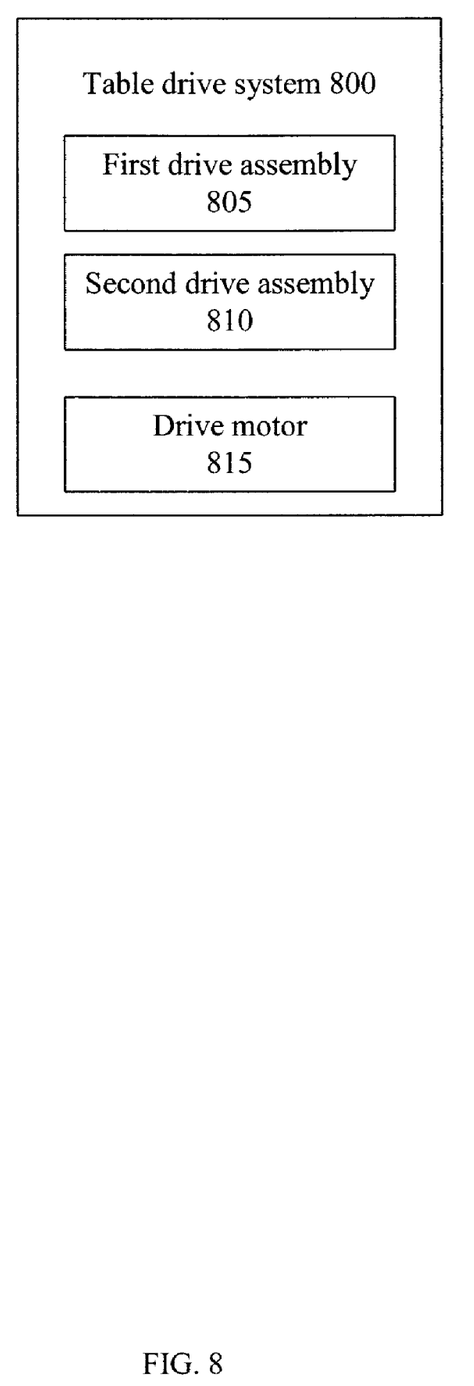
FIG. 8 shows a block diagram of an example of a table drive system in an embodiment of the invention.

In yet another embodiment as shown in FIG. 8, a table drive system 800 comprising a first drive assembly 805, similar to the first drive assembly 205 described above, adapted for moving a support table (not shown) in a first direction, a second drive assembly 810, similar to the second drive assembly 210 described above, adapted for moving the support table (not shown) in a second direction and a drive motor 815, similar to the drive motor 215 described above, coupled to the first drive assembly 805 and the second drive assembly 810 is provided. The drive motor 815 can be configured to drive the first drive assembly 805 and the second drive assembly 810.

Figure 9:
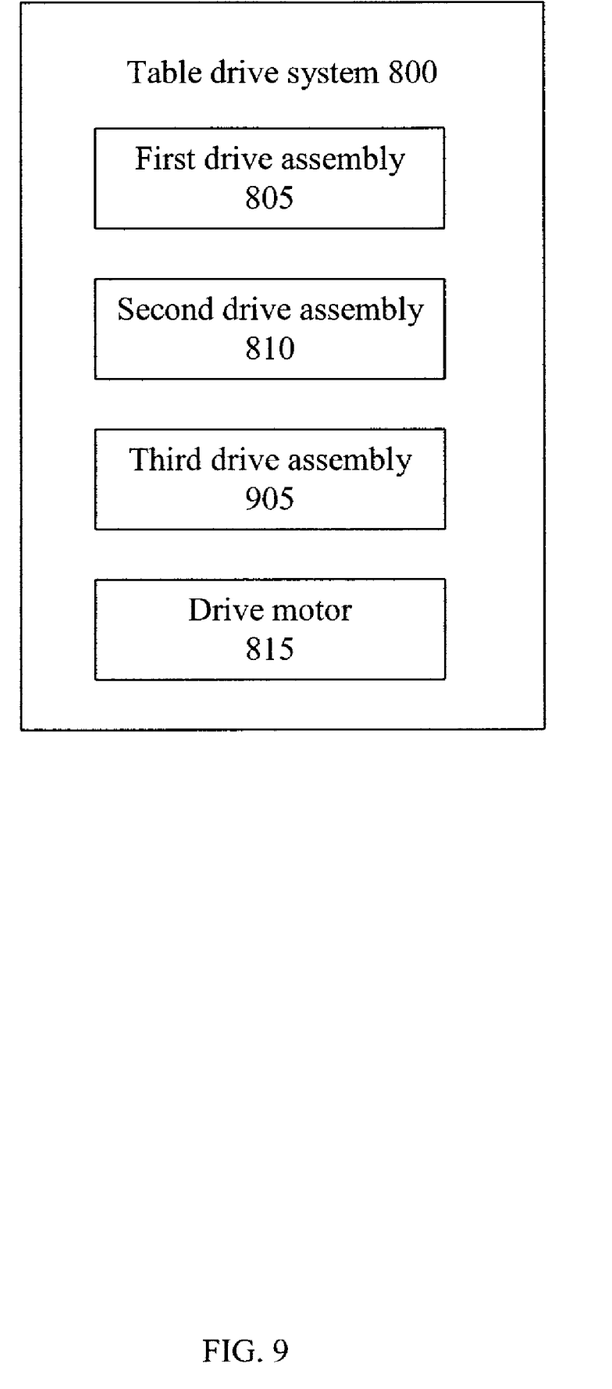
FIG. 9 shows another block diagram of an example of the table drive system in another embodiment of the invention.

In another embodiment, as depicted in FIG. 9, the table drive system 800 may further comprise a third drive assembly 905 adapted for moving the support table (not shown) in a third direction and the drive motor 815 can be configured to drive the third drive assembly 905.

Each of the first drive assembly 805, the second drive assembly 810 and the third drive assembly 905 of the table drive system 800 may further comprise a coupling device, a brake device and a feedback device using which the drive assemblies 805, 810 and 905 can be coupled to the drive motor 815. The coupling device provides a selective transmission system, the feedback device provides a greater positioning accuracy whereas the brake device provides a better safety and imparts a robust design feature to the table drive system 800.

The invention provides a simple, compact, reliable, serviceable and accurate patient positioning system 120 comprising a single drive motor 215 for driving multiple drive assemblies 205, 210 and 305. This eliminates the use of multiple drive motors and facilitates cost effectiveness.

The drive system 600 comprising a single drive motor 215 facilitates optimum utilization of the drive motor 215 in terms of functioning and idle time.

The necessity of using multiple drive motors is eliminated thereby reducing the number of components utilized in the drive system 600. The reduced number of components leads to improvement in assemble time, increased space for convenience in assembling other parts and lower weight of the drive system 600. As a result of this, the patient positioning system 120 can be sleek with better aesthetics. Reducing the number of components can further help in enhancing the reliability of the patient positioning system 120.

In various embodiments of the invention, a drive system for a patient positioning system and a patient positioning system using a drive system are described. However, the embodiments are not limited and may be implemented in connection with different applications. The application of the invention can be extended to other areas, for example positioning devices. The invention provides a broad concept of using a single drive motor to drive multiple drive assemblies, which can be adapted in a similar positioning system. The design can be carried further and implemented in various forms and specifications.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A table drive system comprising: a first drive assembly configured for moving a support table in a first direction, a second drive assembly configured for moving the support table in a second direction, and a drive motor coupled to the first drive assembly and the second drive assembly, wherein the drive motor is configured to drive the first drive assembly and the second drive assembly, and the first direction comprises a longitudinal direction and the second direction comprises a lateral direction.

2. The table drive system of claim 1, wherein the first drive assembly comprises a screw drive assembly.

3. A table drive system comprising: a first drive assembly configured for moving a support table in a first direction, a second drive assembly configured for moving the support table in a second direction, a third drive assembly configured for moving the support table in a third direction, and a drive motor coupled to the first drive assembly, the second drive assembly and the third drive assembly, wherein the drive motor is configured to drive the first drive assembly, the second drive assembly and the third drive assembly.

4. The table drive system of claim 3, wherein the first direction comprises a longitudinal direction, the second direction comprises a lateral direction and the third direction comprises a vertical direction.

5. The table drive system of claim 3, wherein the third drive assembly comprises a cross bar drive assembly.

6. The table drive system of claim 3, further comprising a plurality of coupling device, wherein each coupling device is coupled to the drive motor at a first end and one of the first drive assembly, the second drive assembly and the third drive assembly at a second end.

7. The table drive system of claim 3, further comprising a plurality of brake device, wherein each brake device is coupled to one of the first drive assembly, the second drive assembly and the third drive assembly.

8. The table drive system of claim 3, further comprising a plurality of feedback device, wherein each feedback device is coupled to one of the first drive assembly, the second drive assembly and the third drive assembly.

9. The table drive system of claim 8, wherein the feedback device is an absolute encoder.

10. A table drive system comprising: a first drive assembly configured for moving a support table in a first direction, a second drive assembly configured for moving the support table in a second direction, and a drive motor coupled to the first drive assembly and the second drive assembly, wherein the drive motor is configured to drive the first drive assembly and the second drive assembly, and the second drive assembly comprises a rack and pinion drive assembly.

11. A drive system for a patient positioning system, the drive system comprising:
at least two driving members configured for moving a patient support table, wherein a first of the at least two driving members is configured for moving the patient support table in a longitudinal direction and a second of the at least two driving members is configured for moving the patient support table in a lateral direction; and
a drive motor coupled to the at least two driving members, wherein the drive motor is configured to drive the at least two driving members.

12. The drive system of claim 11, wherein a first of the at least two driving members comprises a screw drive assembly.

13. A drive system for a patient positioning system, the drive system comprising: at least two driving members configured for moving a patient support table; and a drive motor coupled to the at least two driving members, wherein the drive motor is configured to drive the at least two driving members, and a second of the at least two driving members comprises a rack and pinion drive assembly.

14. A drive system for a patient positioning system comprising: at least three driving members configured for moving a patient support table; and a drive motor coupled to the at least three driving members, wherein the drive motor is configured to drive the at least three driving members.

15. The drive system of claim 14, wherein the third driving member comprises a cross bar drive assembly.

16. A patient positioning system comprising: a patient support table; a first drive assembly adapted for moving the patient support table in a first direction, a second drive assembly adapted for moving the patient support table in a second direction and a drive motor in combination with the first drive assembly and the second drive assembly, wherein the drive motor is configured to drive the first drive assembly and the second drive assembly, and the first direction comprises an X-axis direction and the second direction comprises a Y-axis direction.

17. The patient positioning system of claim 16, wherein the first drive assembly comprises a screw drive assembly.

18. A patient positioning system comprising; a patient support table; a first drive assembly adapted for moving the patient support table in a first direction, a second drive assembly adapted for moving the patient support table in a second direction, a third drive assembly adapted for moving the patient support table in a third direction, and a drive motor in combination with the first drive assembly, the second drive assembly and the third drive assembly, wherein the drive motor is configured to drive the first drive assembly, the second drive assembly and the third drive assembly.

19. The patient positioning system of claim 18, wherein the first drive assembly is adapted for moving the patient support table along a longitudinal axis, the second drive assembly is adapted for moving the patient support table along a lateral axis and the third drive assembly is adapted for moving the patient support table along a vertical axis.

20. The patient positioning system of claim 18, wherein the third drive assembly comprises a cross bar drive assembly.

21. A patient positioning system comprising: a patient support table; a first drive assembly adapted for moving the patient support table in a first direction, a second drive assembly adapted for moving the patient support table in a second direction, and a drive motor in combination with the first drive assembly and the second drive assembly, wherein the drive motor is configured to drive the first drive assembly and the second drive assembly, and the second drive assembly comprises a rack and pinion drive assembly.

* * * * *